(12) United States Patent
Zhang et al.

(10) Patent No.: US 10,481,065 B2
(45) Date of Patent: Nov. 19, 2019

(54) METHODS AND SYSTEMS FOR EXHAUST PARTICULATE MATTER SENSING

(71) Applicant: Ford Global Technologies, LLC, Dearborn, MI (US)

(72) Inventors: Xiaogang Zhang, Novi, MI (US); David Charles Weber, Toledo, OH (US); Vidhushekhar Zambare, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 85 days.

(21) Appl. No.: 15/909,719

(22) Filed: Mar. 1, 2018

(65) Prior Publication Data

US 2019/0271629 A1 Sep. 5, 2019

(51) Int. Cl.
*F01N 13/00* (2010.01)
*G01N 15/06* (2006.01)
*F01N 3/031* (2006.01)
*F01N 11/00* (2006.01)
*F01N 3/033* (2006.01)

(52) U.S. Cl.
CPC ......... *G01N 15/0618* (2013.01); *F01N 3/031* (2013.01); *F01N 3/033* (2013.01); *F01N 11/002* (2013.01); *F01N 2550/04* (2013.01); *F01N 2560/05* (2013.01); *F01N 2900/0416* (2013.01)

(58) Field of Classification Search
CPC ............... F01N 13/008; F01N 2240/20; F01N 2560/05; F01N 2560/20; G01N 15/0606; G01N 15/0618; G01N 15/0643
See application file for complete search history.

(56) References Cited

U.S. PATENT DOCUMENTS

| | | | |
|---|---|---|---|
| 8,225,648 | B2 | 7/2012 | Nelson |
| 2011/0232268 | A1 | 9/2011 | Nelson |
| 2015/0047330 | A1* | 2/2015 | Zhang ..................... F01N 3/02 60/311 |
| 2015/0355067 | A1 | 12/2015 | Zhang et al. |
| 2016/0131013 | A1 | 5/2016 | Yi et al. |
| 2016/0320285 | A1* | 11/2016 | Weber ............... G01N 15/0656 |
| 2017/0146430 | A1 | 5/2017 | Zhang |
| 2017/0146440 | A1 | 5/2017 | Zhang |
| 2017/0276102 | A1 | 9/2017 | Zhang et al. |
| 2018/0100423 | A1 | 4/2018 | Zhang |
| 2018/0100424 | A1 | 4/2018 | Zhang |
| 2018/0217045 | A1* | 8/2018 | Tiefenbach ............ G01N 15/06 |

* cited by examiner

*Primary Examiner* — Jonathan R Matthias
(74) *Attorney, Agent, or Firm* — Geoffrey Brumbaugh; McCoy Russell LLP (57) ABSTRACT

Methods and systems are provided for a PM sensor. In one example, a method comprises flowing exhaust gas to a cone-shaped PM sensor having a pair of openings arranged across from one another and a plurality of outlets distal to the pair of openings.

20 Claims, 7 Drawing Sheets

METHODS AND SYSTEMS FOR EXHAUST PARTICULATE MATTER SENSING

FIELD

The present description relates generally to particle matter (PM) sensors in an exhaust gas flow.

BACKGROUND/SUMMARY

Combustion exhaust is a regulated emission. Particulate matter (PM), is the particulate component of exhaust, which includes soot and aerosols such as ash particulates, metallic abrasion particles, sulfates, and silicates. When released into the atmosphere, PMs can take the form of individual particles or chain aggregates, with most in the invisible submicrometer range of 100 nanometers. Various technologies have been developed for identifying and filtering out exhaust PMs before the exhaust is released to the atmosphere.

As an example, soot sensors, also known as PM sensors, may be used in vehicles having internal combustion engines. A PM sensor may be located upstream and/or downstream of a particulate filter (PF), and may be used to sense PM loading on the filter and diagnose operation of the PF. The PM sensor may sense a particulate matter or soot load based on a correlation between a measured change in electrical conductivity (or resistivity) between a pair of electrodes placed on a substrate surface of the sensor with the amount of PM deposited between the measuring electrodes. Specifically, the measured conductivity may provide a measure of soot accumulation. As such, the sensitivity of the PM sensors to measure PM in the exhaust may depend on the exhaust flow rate, with increased exhaust flow rate leading to increased PM sensor sensitivity and decreased exhaust flow rate resulting in decreased PM sensor sensitivity. With this increased dependence on exhaust flow rate, the PM sensor capturing the PMs exiting the PF, may not truly reflect the PF filtering capabilities. Furthermore, PM sensors may be prone to contamination from impingement of water droplets and/or larger particulates present in the exhaust gases, thus affecting the PM sensor sensitivity and leading to errors in the output of the PM sensor.

One example PM sensor design is shown by Nelson in U.S. Pat. No. 8,225,648B2. Therein, a PM sensor includes a flow redirector and a barrier positioned around a PM sensor element to filter out the larger particulates from impinging the PM sensor element. The barrier thus serves to block larger particulates in the exhaust flow from impinging on the PM sensor element, thereby reducing PM sensor sensitivity fluctuations due to large particulates depositing on the PM sensor element.

In one example, the issues described above may be addressed by a method for flowing exhaust gas proximal to a central axis of an exhaust passage through a first opening of a cone-shaped soot sensor; expelling a first portion of the exhaust gas through a second opening directly across the first opening, and diverting a second portion of the exhaust gas around flow diverters spaced about electrodes distal to the central axis. In this way, the second opening may expel larger particulates to increase an accuracy of the sensor.

As one example, the flow diverters may further prevent larger particulates from accumulating onto the substrate. The flow diverters may be strategically spaced away from one or more surfaces of the soot sensor, based on constituents produced, such that larger particulates may entropically oppose flowing passed the flow diverters to the substrate. Additionally, by arranging the first opening along the central axis of the exhaust passage, the soot sensor may receive sufficient exhaust gas flow during a plurality of engine operating conditions. By doing this, low exhaust gas flow and larger particulate impingement may be at least partially avoided.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 2A-2D are shown approximately to scale.

DETAILED DESCRIPTION

Figure 3:
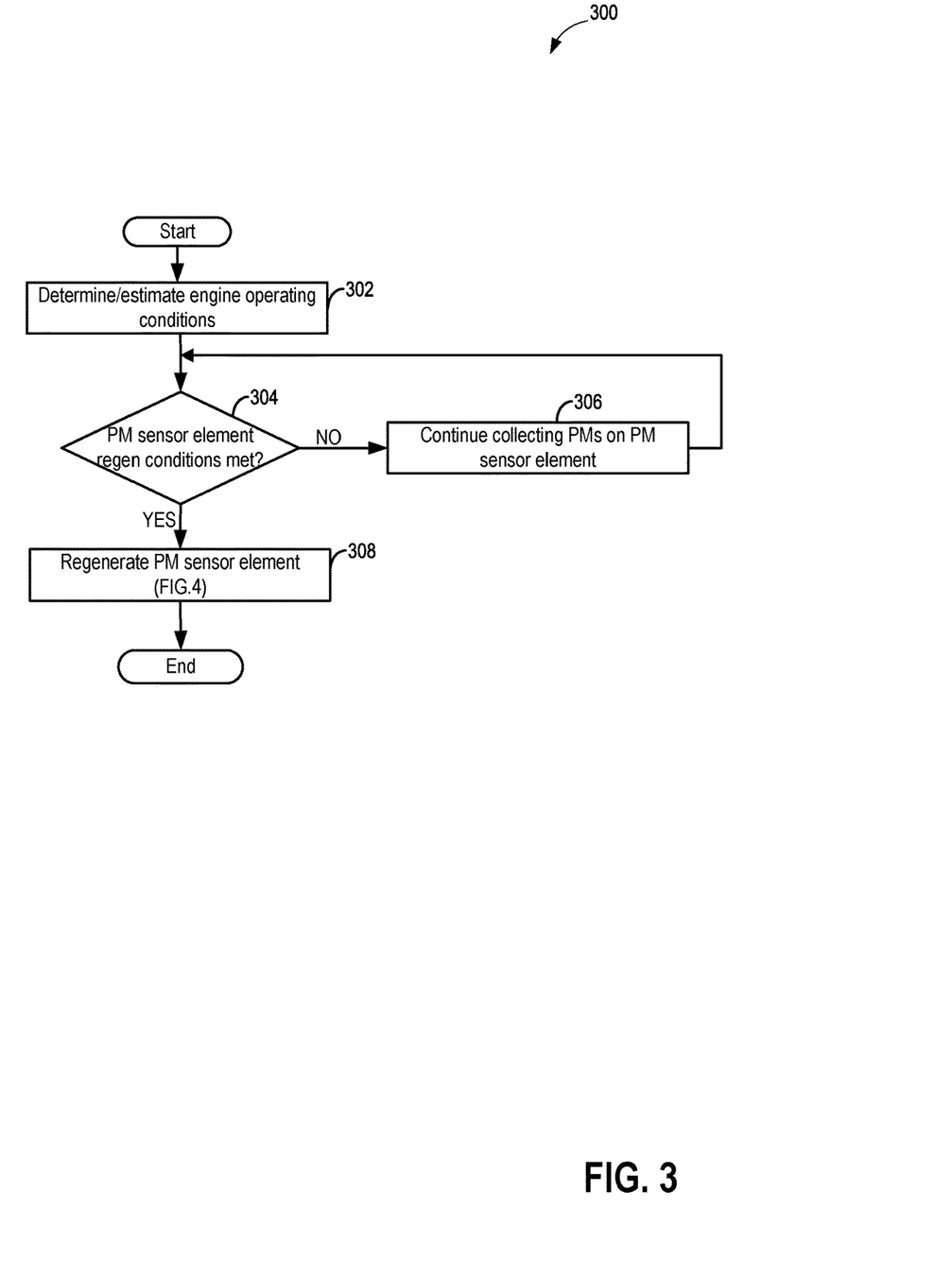
FIG. 3 shows a flow chart depicting a method for determining if PM sensor element regeneration conditions are met.
Figure 4:
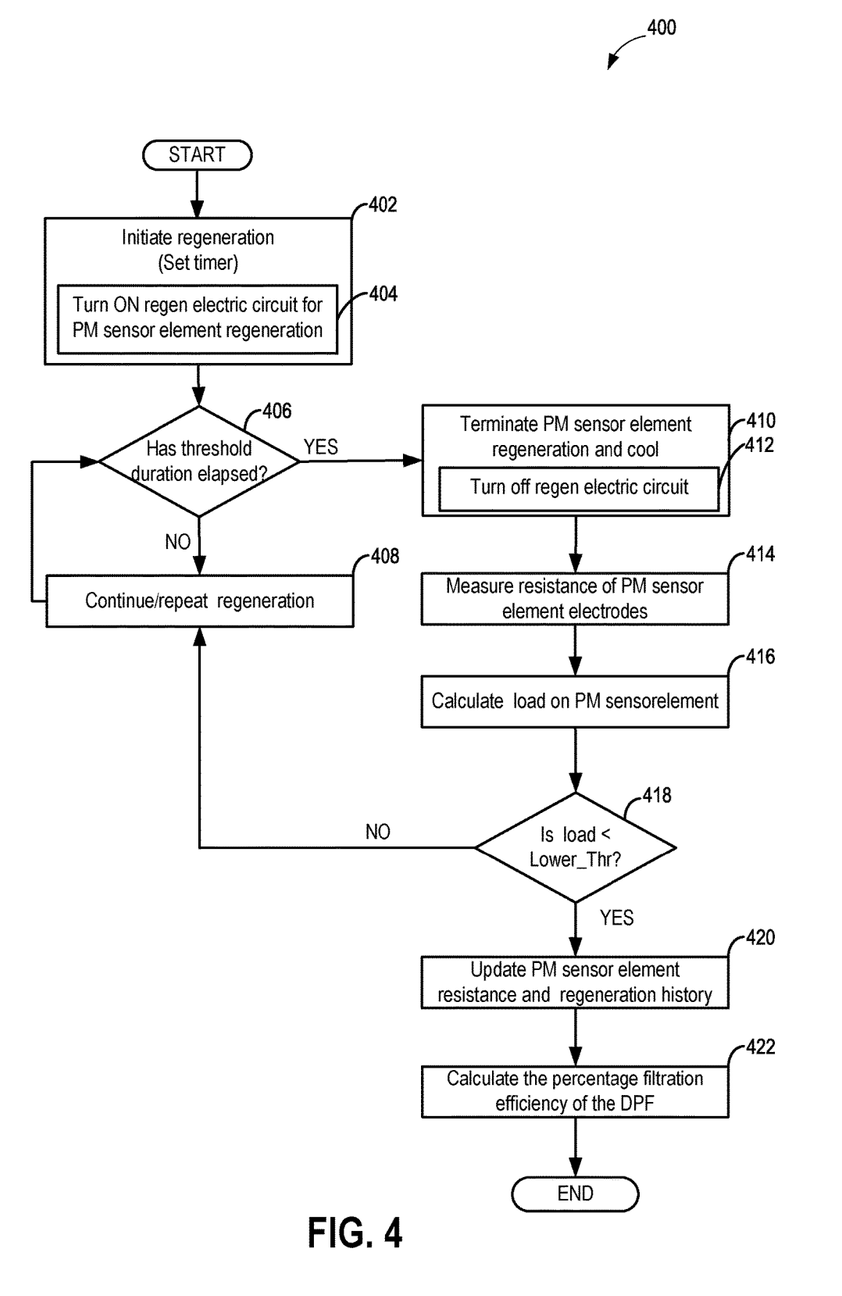
FIG. 4 shows a chart depicting a method for performing regeneration of the PM sensor.
Figure 5:
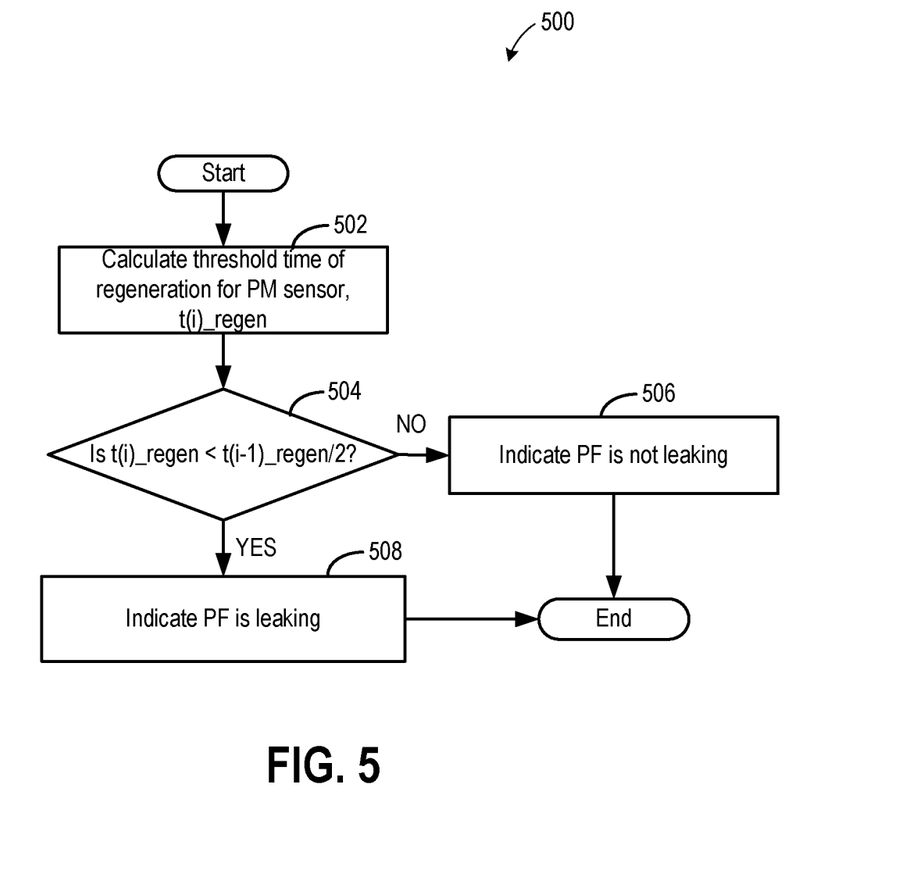
FIG. 5 shows a flow chart depicting a method for diagnosing leaks in a particulate filter positioned upstream of the PM sensor.

The following description relates to systems and methods for a PM sensor. The PM sensor may be arranged in an exhaust passage coupled to an engine of a hybrid vehicle, such as the hybrid vehicle of FIG. 1. The PM sensor may comprise one or more features to increase an accuracy of the PM sensor. These features are illustrated in FIGS. 2A and 2B. The PM sensor may comprise one or more openings for admitting and expelling exhaust gases. These openings may be arranged such that the PM sensor may capture a sufficient amount of exhaust gas while allowing momentum of larger particulates in the exhaust gas to flow out of the PM sensor without depositing onto a substrate arranged therein. The substrate may comprise two surfaces as shown in FIGS. 2C and 2D. A first surface of the substrate may be coupled to a pair of electrodes and a second surface of the substrate may be coupled to a heating element. The substrate may be warm-up by the heating element, wherein the particulates accumulated thereon may be burned off. A method for determining if regeneration conditions of the PM sensor are met is shown in FIG. 3. A method for implementing the regeneration is shown in FIG. 4. A method for determining a condition of a PF arranged upstream of the PM sensor is shown in FIG. 5.

Figure 1:
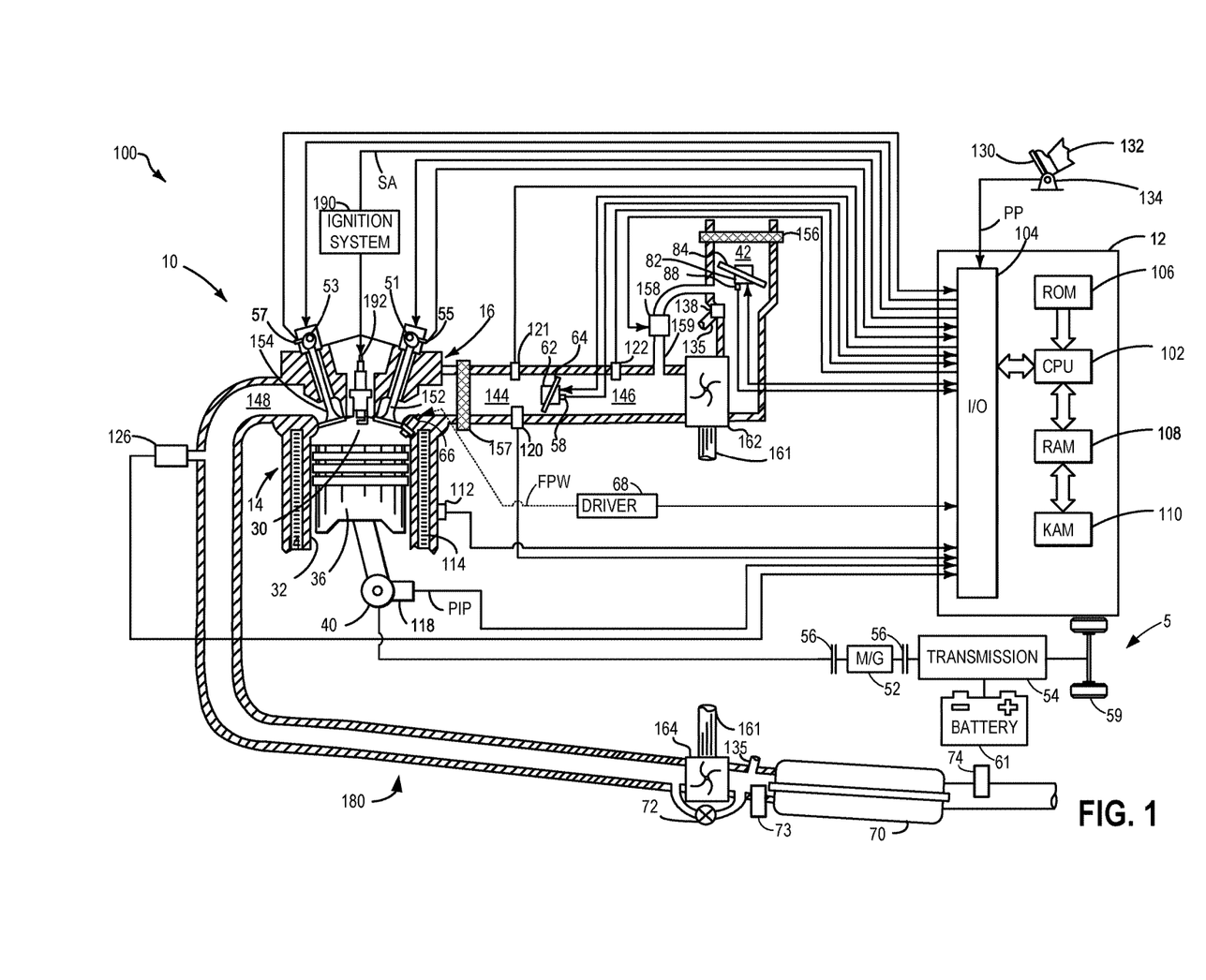
FIG. 1 shows a schematic of an engine for a hybrid vehicle.
Figure 2A:
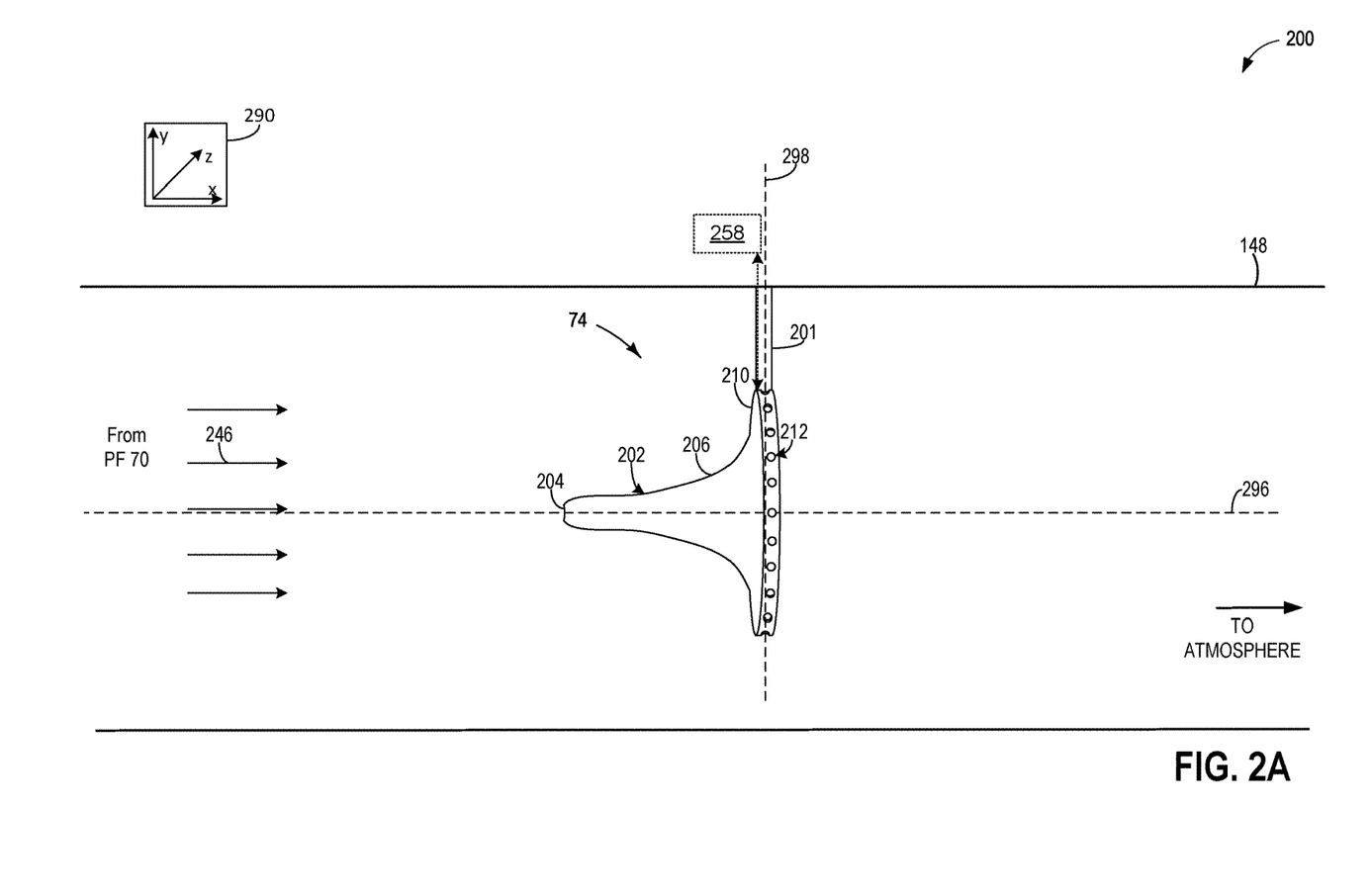
FIG. 2A shows a perspective view of a PM sensor.
Figure 2B:
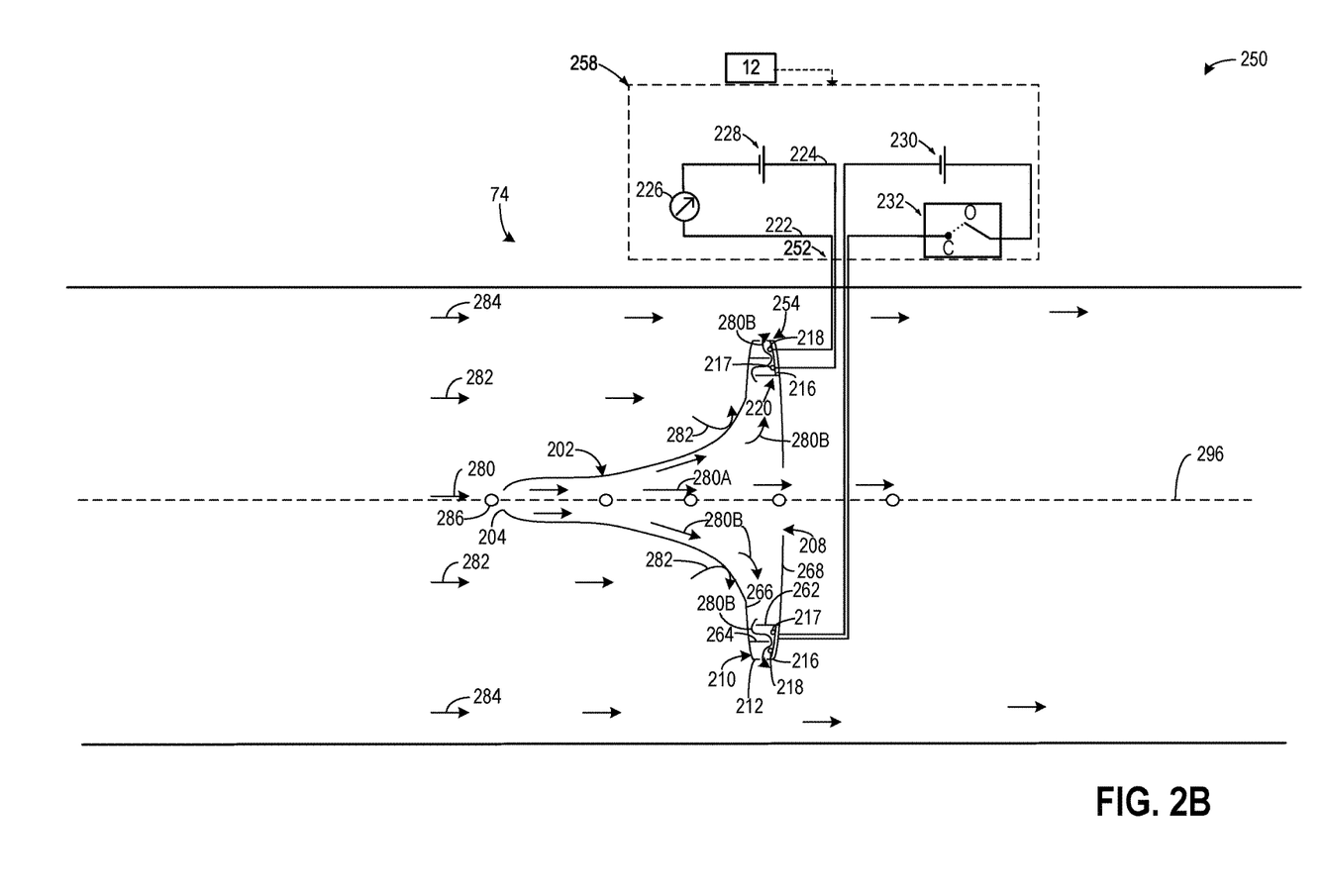
FIG. 2B shows a cross-sectional view of the PM sensor.
Figure 2C:
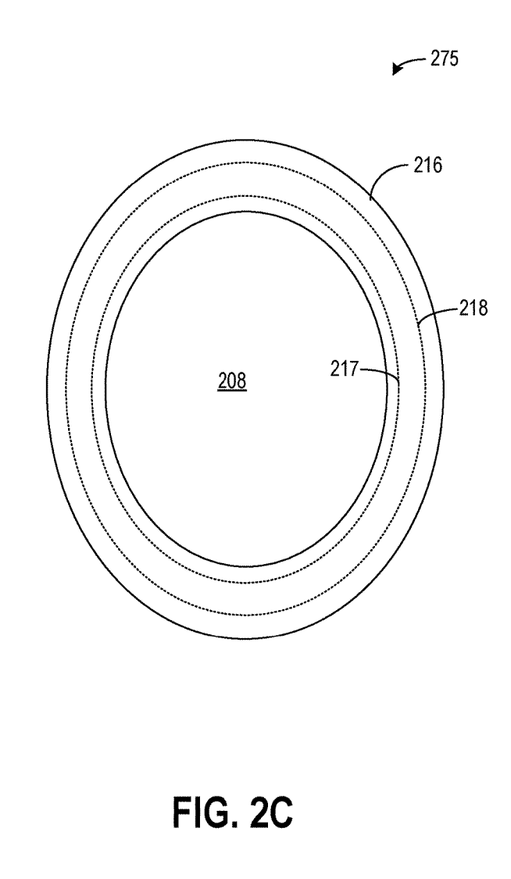
FIG. 2C shows an embodiment of a first surface of a substrate of the PM sensor.
Figure 2D:
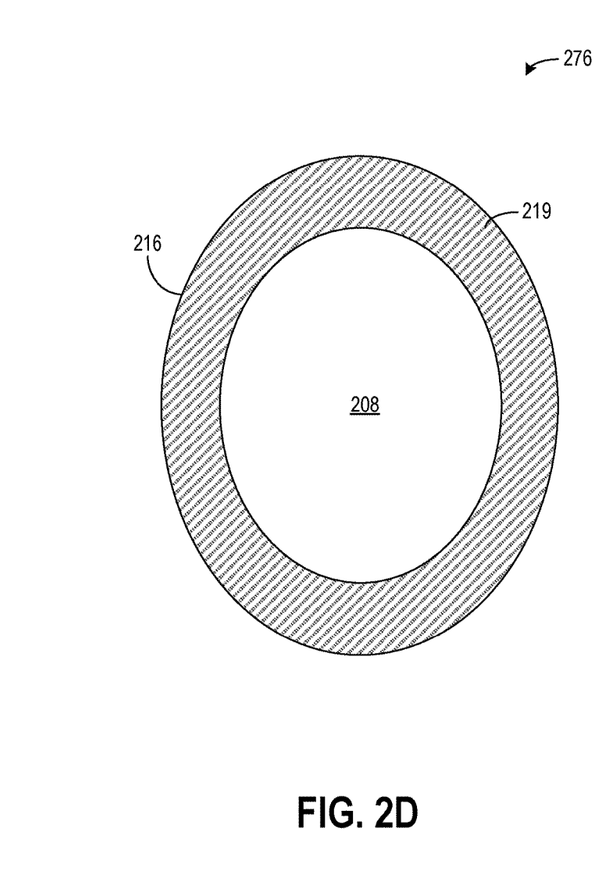
FIG. 2D shows an embodiment of a second surface of the substrate of the PM sensor.

FIGS. 1-2D show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. It will be appreciated that one or more components referred to as being "substantially similar and/or identical" differ from one another according to manufacturing tolerances (e.g., within 1-5% deviation).

Note that FIG. 2B shows arrows indicating where there is space for gas to flow, and the solid lines of the device walls show where flow is blocked and communication is not possible due to the lack of fluidic communication created by the device walls spanning from one point to another. The walls create separation between regions, except for openings in the wall which allow for the described fluid communication.

FIG. 1 depicts an engine system 100 for a vehicle. The vehicle may be an on-road vehicle having drive wheels which contact a road surface. Engine system 100 includes engine 10 which comprises a plurality of cylinders. FIG. 1 describes one such cylinder or combustion chamber in detail. The various components of engine 10 may be controlled by electronic engine controller 12.

Engine 10 includes a cylinder block 14 including at least one cylinder bore 20, and a cylinder head 16 including intake valves 152 and exhaust valves 154. In other examples, the cylinder head 16 may include one or more intake ports and/or exhaust ports in examples where the engine 10 is configured as a two-stroke engine. The cylinder block 14 includes cylinder walls 32 with piston 36 positioned therein and connected to crankshaft 40. Thus, when coupled together, the cylinder head 16 and cylinder block 14 may form one or more combustion chambers. As such, the combustion chamber 30 volume is adjusted based on an oscillation of the piston 36. Combustion chamber 30 may also be referred to herein as cylinder 30. The combustion chamber 30 is shown communicating with intake manifold 144 and exhaust manifold 148 via respective intake valves 152 and exhaust valves 154. Each intake and exhaust valve may be operated by an intake cam 51 and an exhaust cam 53. Alternatively, one or more of the intake and exhaust valves may be operated by an electromechanically controlled valve coil and armature assembly. The position of intake cam 51 may be determined by intake cam sensor 55. The position of exhaust cam 53 may be determined by exhaust cam sensor 57. Thus, when the valves 152 and 154 are closed, the combustion chamber 30 and cylinder bore 20 may be fluidly sealed, such that gases may not enter or leave the combustion chamber 30.

Combustion chamber 30 may be formed by the cylinder walls 32 of cylinder block 14, piston 36, and cylinder head 16. Cylinder block 14 may include the cylinder walls 32, piston 36, crankshaft 40, etc. Cylinder head 16 may include one or more fuel injectors such as fuel injector 66, one or more intake valves 152, and one or more exhaust valves such as exhaust valves 154. The cylinder head 16 may be coupled to the cylinder block 14 via fasteners, such as bolts and/or screws. In particular, when coupled, the cylinder block 14 and cylinder head 16 may be in sealing contact with one another via a gasket, and as such may the cylinder block 14 and cylinder head 16 may seal the combustion chamber 30, such that gases may only flow into and/or out of the combustion chamber 30 via intake manifold 144 when intake valves 152 are opened, and/or via exhaust manifold 148 when exhaust valves 154 are opened. In some examples, only one intake valve and one exhaust valve may be included for each combustion chamber 30. However, in other examples, more than one intake valve and/or more than one exhaust valve may be included in each combustion chamber 30 of engine 10.

In some examples, each cylinder of engine 10 may include a spark plug 192 for initiating combustion. Ignition system 190 can provide an ignition spark to cylinder 14 via spark plug 192 in response to spark advance signal SA from controller 12, under select operating modes. However, in some embodiments, spark plug 192 may be omitted, such as where engine 10 may initiate combustion by auto-ignition or by injection of fuel as may be the case with some diesel engines.

Fuel injector 66 may be positioned to inject fuel directly into combustion chamber 30, which is known to those skilled in the art as direct injection 30. Fuel injector 66 delivers liquid fuel in proportion to the pulse width of signal FPW from controller 12. Fuel is delivered to fuel injector 66 by a fuel system (not shown) including a fuel tank, fuel pump, and fuel rail. Fuel injector 66 is supplied operating current from driver 68 which responds to controller 12. In some examples, the engine 10 may be a gasoline engine, and the fuel tank may include gasoline, which may be injected by injector 66 into the combustion chamber 30. However, in other examples, the engine 10 may be a diesel engine, and the fuel tank may include diesel fuel, which may be injected by injector 66 into the combustion chamber. Further, in such examples where the engine 10 is configured as a diesel engine, the engine 10 may include a glow plug to initiate combustion in the combustion chamber 30.

Intake manifold 144 is shown communicating with throttle 62 which adjusts a position of throttle plate 64 to control airflow to engine cylinder 30. This may include controlling airflow of boosted air from intake boost chamber 146. In some embodiments, throttle 62 may be omitted and airflow to the engine may be controlled via a single air intake system throttle (AIS throttle) 82 coupled to air intake passage 42 and located upstream of the intake boost chamber 146. In yet further examples, throttle 82 may be omitted and airflow to the engine may be controlled with the throttle 62.

In some embodiments, engine 10 is configured to provide exhaust gas recirculation, or EGR. When included, EGR may be provided as high-pressure EGR and/or low-pressure EGR. In examples where the engine 10 includes low-pressure EGR, the low-pressure EGR may be provided via EGR passage 135 and EGR valve 138 to the engine air intake system at a position downstream of air intake system (AIS) throttle 82 and upstream of compressor 162 from a location in the exhaust system downstream of turbine 164. EGR may be drawn from the exhaust system to the intake air system when there is a pressure differential to drive the flow. A pressure differential can be created by partially closing AIS throttle 82. Throttle plate 84 controls pressure at the inlet to compressor 162. The AIS may be electrically controlled and its position may be adjusted based on optional position sensor 88.

Ambient air is drawn into combustion chamber 30 via intake passage 42, which includes air filter 156. Thus, air first enters the intake passage 42 through air filter 156. Compressor 162 then draws air from air intake passage 42 to supply boost chamber 146 with compressed air via a compressor outlet tube (not shown in FIG. 1). In some examples, air intake passage 42 may include an air box (not shown) with a filter. In one example, compressor 162 may be a turbocharger, where power to the compressor 162 is drawn from the flow of exhaust gases through turbine 164. Specifically, exhaust gases may spin turbine 164 which is coupled to compressor 162 via shaft 161. A wastegate 72 allows exhaust gases to bypass turbine 164 so that boost pressure can be controlled under varying operating conditions. Wastegate 72 may be closed (or an opening of the wastegate may be decreased) in response to increased boost demand, such as during an operator pedal tip-in. By closing the wastegate, exhaust pressures upstream of the turbine can be increased, raising turbine speed and peak power output. This allows boost pressure to be raised. Additionally, the wastegate can be moved toward the closed position to maintain desired boost pressure when the compressor recirculation valve is partially open. In another example, wastegate 72 may be opened (or an opening of the wastegate may be increased) in response to decreased boost demand, such as during an operator pedal tip-out. By opening the wastegate, exhaust pressures can be reduced, reducing turbine speed and turbine power. This allows boost pressure to be lowered.

However, in alternate embodiments, the compressor 162 may be a supercharger, where power to the compressor 162 is drawn from the crankshaft 40. Thus, the compressor 162 may be coupled to the crankshaft 40 via a mechanical linkage such as a belt. As such, a portion of the rotational energy output by the crankshaft 40, may be transferred to the compressor 162 for powering the compressor 162.

Compressor recirculation valve 158 (CRV) may be provided in a compressor recirculation path 159 around compressor 162 so that air may move from the compressor outlet to the compressor inlet so as to reduce a pressure that may develop across compressor 162. A charge air cooler 157 may be positioned in boost chamber 146, downstream of compressor 162, for cooling the boosted aircharge delivered to the engine intake. However, in other examples as shown in FIG. 1, the charge air cooler 157 may be positioned downstream of the electronic throttle 62 in an intake manifold 144. In some examples, the charge air cooler 157 may be an air to air charge air cooler. However, in other examples, the charge air cooler 157 may be a liquid to air cooler.

In the depicted example, compressor recirculation path 159 is configured to recirculate cooled compressed air from downstream of charge air cooler 157 to the compressor inlet. In alternate examples, compressor recirculation path 159 may be configured to recirculate compressed air from downstream of the compressor and upstream of charge air cooler 157 to the compressor inlet. CRV 158 may be opened and closed via an electric signal from controller 12. CRV 158 may be configured as a three-state valve having a default semi-open position from which it can be moved to a fully-open position or a fully-closed position.

Universal Exhaust Gas Oxygen (UEGO) sensor 126 is shown coupled to exhaust manifold 148 upstream of emission control device 70. Alternatively, a two-state exhaust gas oxygen sensor may be substituted for UEGO sensor 126. Emission control device 70 may include multiple catalyst bricks, in one example. In another example, multiple emission control devices, each with multiple bricks, can be used. While the depicted example shows UEGO sensor 126 upstream of turbine 164, it will be appreciated that in alternate embodiments, UEGO sensor may be positioned in the exhaust manifold downstream of turbine 164 and upstream of Emission control device 70. Additionally or alternatively, the converter 70 may comprise a diesel oxidation catalyst (DOC) and/or a diesel cold-start catalyst.

Herein, the emission control device 70 is a particulate filter (PF) 70. The PF 70 may comprise one or more other catalyst including a three-way catalyst, $NO_x$ trap, selective catalytic reduction device, and combinations thereof. The PF 70 may be manufactured from a variety of materials including cordierite, silicon carbide, and other high temperature oxide ceramics. The PF 70 may be periodically regenerated in order to reduce soot deposits in the filter that resist exhaust gas flow. Filter regeneration may be accomplished by heating the filter to a temperature that will burn soot particles at a faster rate than the deposition of new soot particles, for example, 400-600° C.

A first particulate matter (PM) sensor 73 may be arranged upstream of the PF 70 in the exhaust passage 148. Additionally or alternatively, a second PM sensor 74 may be arranged downstream of the PF 70 in the exhaust passage 148. Herein, the PM sensor 74 may be interchangeably referred to as soot sensor 74. The PM sensors 73, 74 may diagnose a condition of the PF 70 based on a particulate load. The first PM sensor 73 may diagnose a condition of the PF 70 based on a concentration of soot flowing to the PF 70. Data stored in a multi-input loop up table may be used to extrapolate the concentration of soot flowing to the PF 70 and a predicted degradation and/or longevity of the PF 70. Alternatively, the second PM sensor 74 may diagnose a condition of the PF 70 based on a concentration of soot flowing out of the PF 70. The PM sensor 74 will be described in greater detail below.

Controller 12 is shown in FIG. 1 as a microcomputer including: microprocessor unit 102, input/output ports 104, read-only memory 106, random access memory 108, keep alive memory 110, and a conventional data bus. Controller 12 is shown receiving various signals from sensors coupled to engine 10, in addition to those signals previously discussed, including: engine coolant temperature (ECT) from temperature sensor 112 coupled to cooling sleeve 114; a position sensor 134 coupled to an input device 130 for sensing input device pedal position (PP) adjusted by a vehicle operator 132; a knock sensor for determining ignition of end gases (not shown); a measurement of engine manifold pressure (MAP) from pressure sensor 121 coupled to intake manifold 144; a measurement of boost pressure from pressure sensor 122 coupled to boost chamber 146; an engine position sensor from a Hall effect sensor 118 sensing crankshaft 40 position; a measurement of air mass entering the engine from sensor 120 (e.g., a hot wire air flow meter); and a measurement of throttle position from sensor 58. Barometric pressure may also be sensed (sensor not shown) for processing by controller 12. In a preferred aspect of the present description, Hall effect sensor 118 produces a predetermined number of equally spaced pulses every revolution of the crankshaft from which engine speed (RPM) can be determined. The input device 130 may comprise an accelerator pedal and/or a brake pedal. As such, output from the position sensor 134 may be used to determine the position of the accelerator pedal and/or brake pedal of the input device 130, and therefore determine a desired engine torque. Thus, a desired engine torque as requested by the vehicle operator 132 may be estimated based on the pedal position of the input device 130.

In some examples, vehicle 5 may be a hybrid vehicle with multiple sources of torque available to one or more vehicle wheels 59. In other examples, vehicle 5 is a conventional vehicle with only an engine, or an electric vehicle with only electric machine(s). In the example shown, vehicle 5 includes engine 10 and an electric machine 61. Electric machine 61 may be a motor or a motor/generator. Crankshaft 40 of engine 10 and electric machine 61 are connected via a transmission 54 to vehicle wheels 59 when one or more clutches 56 are engaged. In the depicted example, a first clutch 56 is provided between crankshaft 40 and electric machine 61, and a second clutch 56 is provided between electric machine 61 and transmission 54. Controller 12 may send a signal to an actuator of each clutch 56 to engage or disengage the clutch, so as to connect or disconnect crankshaft 40 from electric machine 61 and the components connected thereto, and/or connect or disconnect electric machine 61 from transmission 54 and the components connected thereto. Transmission 54 may be a gearbox, a planetary gear system, or another type of transmission. The powertrain may be configured in various manners including as a parallel, a series, or a series-parallel hybrid vehicle.

Electric machine 61 receives electrical power from a traction battery 58 to provide torque to vehicle wheels 59. Electric machine 61 may also be operated as a generator to provide electrical power to charge battery 58, for example during a braking operation.

The controller 12 receives signals from the various sensors of FIG. 1 and employs the various actuators of FIG. 1 to adjust engine operation based on the received signals and instructions stored on a memory of the controller. For example, adjusting a fuel injection may include adjusting an actuator of the injector 66 to move to or away from a nozzle of the injector 66 so that fuel may flow to the combustion chamber 30. As another example, adjusting a temperature may include adjusting an actuator of a heating element arranged in the PM sensor 74 to decrease a soot load of the PM sensor (also referred to as sensor heater REGEN, or sensor tip soot cleaning). Additionally, the PM sensor may provide feedback regarding a condition of the PF 70. After the sensor soot tip cleaning operation, the sensor then collects soot at a rate that may be based on a function of the exhaust soot concentration and of the exhaust flow rate. Thus, a duration of accumulation of the soot on the electrodes before a second regeneration occurs within a threshold duration of a first regeneration of the PM sensor 74, which may indicate that the PF 70 may be degraded (e.g., cracked) and leaking soot. Thus, the threshold duration may be based on an amount of time between successive regenerations, wherein if a time elapsed between the regenerations is less than the threshold duration then the PF 70 is indicated degraded. If the amount of time is greater than the threshold duration then the PF 70 may not be degraded. As such, the controller 12 may alert the driver that a leak condition is occurring in the PF via an indicator lamp or the like, such that one or more driving parameters may be adjusted (e.g., fueling may decrease, air/fuel ratio may increase, engine torque output may decrease) until the leak condition is removed.

For detection of feedgas soot concentrations upstream of the PF using a PM sensor in the feedgas location, the controller 12 may adjust engine operating parameters by adjusting an actuator of a fuel injector to adjust the fuel injector to inject fuel in a way to inject less soot or it may adjust the EGR valve to create less soot in the combustion chamber, or other means of engine and hybrid power control. Additionally or alternatively, engine power output may decrease and power consumption from the battery 58 may increase to mitigate soot production.

Turning now to FIG. 2A, a schematic view of an example embodiment 200 of the particulate matter (PM) sensor 74 of FIG. 1 is shown. As such, components previously introduced may be similarly numbered in subsequent figures. While the description below is in regard to PM sensor 74, it will be appreciated that the description may also apply to PM sensor 73 of FIG. 1 without departing from the scope of the present disclosure. The PM sensor 74 may be configured to measure PM mass and/or concentration in the exhaust gas, and as such, may be arranged within exhaust passage 148 upstream or downstream of a particulate filter (such as PF 70 shown in FIG. 1).

As shown in FIG. 1 above and in the embodiment 200 of FIG. 2A, the PM sensor 74 may be disposed inside exhaust passage 148 with exhaust gases flowing from downstream of a particulate filter towards an exhaust tailpipe, as indicated by arrows 246. In one example, arrows 246 are parallel to a general direction of exhaust gas flow in the exhaust passage 148. PM sensor 74 may include an outer shell 202 that may serve to protect a PM sensor element (such as PM sensor element 254 of FIGS. 2B, 2C and 2D) of the PM sensor 74 housed therein and may additionally serve to redirect exhaust gas flow over the PM sensor element as explained below.

An axis system 290 comprising three axes, namely an x-axis parallel to a horizontal direction, a y-axis parallel to a vertical direction, and a z-axis perpendicular to each of the x- and y-axes. The horizontal direction may be substantially parallel to the general direction of exhaust gas (arrows 246). In some examples, a direction of gravity may be parallel to the y-axis. However, due to the symmetry of the PM sensor 74, the PM sensor 74 may be placed in a plurality radial positions along the exhaust passage 148. A first central axis 296 may be a central axis of the exhaust passage 148 and extend in the horizontal direction. A second central axis 298, perpendicular to the first central axis 296, may be a central axis for a disc portion 210 of the PM sensor 74.

The PM sensor 74 may be fixedly arranged in the exhaust passage 148 via a sensor support structure 201. Examples of the sensor support structure 201 may include a pipe, rod, or the like physically coupled to an exhaust pipe of the exhaust passage 148. The physical coupling may include one or more of adhesives, fusions, screws, and welds. Additionally or alternatively, the sensor support structure 201 may be coupled to the exhaust pipe via one or more bosses. In the example of FIG. 2A, the sensor support structure 201 is a hollow pipe. The sensor support structure 201 may be physically coupled to the disc portion 210 of the PM sensor 74. However, the sensor support structure 201 may be physically coupled to other portions of the PM sensor without departing from the scope of the present disclosure.

One or more electrical leads may extend through the sensor support structure 201 to an electric circuit 258. The electric circuit 258 may comprise one or more circuits configured to adjust operation of a regenerating device arranged in the PM sensor element of the PM sensor 74. The sensor support structure 201 may be hermetically sealed from the exhaust passage 148 such that exhaust gas may not contact the electrical leads. This may mitigate degradation to the electrical leads and increase an accuracy of the PM sensor 74. The electric circuit is described in greater detail with respect to FIG. 2B.

The PM sensor 74 may comprise an outer shell 202 housing one or more of the PM sensor 74 components. The outer shell 202 may comprise a cylindrical shape of varying diameter. The diameter may increase in a downstream direction such that the diameter of the outer shell 202 is larger further away from the particulate filter. Additionally or alternatively, the outer shell 202 may decrease in diameter in the downstream direction. In some examples, the outer shell 202 may comprise a horn, cone, cornucopia, or similar shape. Thus, a cross-section of the outer shell 202 taken along a y-z plane may be substantially circular. However, in some examples where the outer shell 202 comprises a square-shaped cross-section in the y-z plane, the outer shell 202 may be a trapezoidal prism or other similar shape.

A rate of increase of the diameter in the downstream direction may be linear, exponential, logarithmic, or the like. In one example, the rate of increase is exponential. As such, the outer shell 202 may comprise a curve or similar deviation from linear such that an angle measured between the central axis 296 and the outer shell 202 may be continuously changing in the downstream direction.

The outer shell 202 may be hollow and configured to admit and expel exhaust gases. More specifically, the outer shell 202 may comprise a first opening 204 arranged at an upstream end of the PM sensor 74 with respect to a direction of exhaust gas flow where a diameter of the outer shell 202 may be smallest. In one example, the first opening 204 is arranged at an apex of the outer shell 202. The first opening 204 may face a direction of incoming exhaust gas (e.g., faces arrow 246) and readily admit exhaust gas flowing proximally to the first central axis 296. The first opening 204 may be arranged on the first central axis 296 such that the first central axis passes through a geometric center of the first opening 204.

An expansion portion 206 may be arranged between the first opening 204 and the disc portion 210. A diameter of the PM sensor 74 corresponding to the expansion portion 206 may increase in the downstream direction such that the disc portion 210 may correspond to a greatest diameter of the PM sensor 74. In one example, a diameter of the disc portion 210 is fixed. The disc portion 210 may comprise at least one second opening 212. A portion of exhaust gas within an interior space of the PM sensor 74 may be expelled via the at least one second opening 212. Herein, the at least one second opening 212 may be interchangeably referred to as a plurality of second openings 212. Each of the plurality of second openings 212 may expel exhaust gas in a different radial direction. That is to say, no two of the second openings may expel exhaust gas in the same direction. Thus, each iteration of the at least one second opening expels exhaust gas in a different direction perpendicular to the general direction of exhaust gas flow (arrows 246).

The at least one second opening 212 may be substantially circular. If a plurality of second openings are arranged on the disc portion 210, then each of the second openings may be circular, oblong, or other similar shapes. Each second opening of the second openings may be equally spaced away from adjacent second openings. Additionally or alternatively, each second opening of the plurality of second openings 212 may be differently shaped and/or sized.

The first opening 204 may be larger than each of the plurality of second openings 212. In some examples, the first opening 204 may be between 0.25 to 1 times an accumulated size of each second opening of the plurality of second openings 212 (e.g., sum of openings of all second openings 212). In one example, a total size of the first opening 204 may be substantially equal to an accumulated size of each second opening of the plurality of second openings 212.

Turning now to FIG. 2B, a cross-sectional embodiment 250 of the PM sensor 74 is shown. The cross-section is parallel to an x-y plane and through the central axis 296. Therein, the electric circuit 258 and an interior of the PM sensor 74 are shown in greater detail.

The PM sensor element 254 includes a pair of planar electrodes 220 forming a concentric structure relative to the first central axis 296. These electrodes may be manufactured from metals such as platinum, gold, osmium, rhodium, iridium, ruthenium, aluminum, titanium, zirconium, and the like, as well as, oxides, cements, alloys and combination comprising at least one of the foregoing metals. The electrodes 220 may be formed on a substrate (e.g., substrate 216 of FIG. 2B) that may comprise highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the pair of electrodes. The spacing between the two electrodes may typically be in the range from 10 micrometers to 100 micrometers. The electrodes 220 extend along and cover a first portion of the substrate 216.

A positive electrode 217 of the pair of electrodes 220 is connected with connecting wires 224 to a positive terminal of a voltage source 228 of the electric circuit 258. A negative electrode 218 of the pair of electrodes 220 is connected to a measurement device 226 via a connecting wire 222, and further connected to a negative terminal of the voltage source 228 of the electric circuit 258. The interconnecting wires 222 and 224, the voltage source 228 and the measurement device 226 are part of the electric circuit 258 and are housed outside the exhaust passage 148 (as one example, <1 meter away). Further, the voltage source 228 and the measurement device of the electric circuit 258 may be controlled by a controller, such as controller 12 of FIG. 1, so that particulate matter collected at the PM sensor may be used for diagnosing leaks in the PF, for example. As such, the measurement device 226 may be any device capable of reading a resistance change across the electrodes, such as a voltmeter. As PM or soot particles get deposited between the electrodes 220, the resistance between the electrode pair may start to decrease, which is indicated by a decrease in the voltage measured by the measurement device 226. The controller 12 may be able to determine the resistance between the electrodes 220 as a function of voltage measured by the measurement device 226 and infer a corresponding PM or soot load on the planar electrodes 220 of the PM sensor 201. By monitoring the load on the PM sensor 201, the exhaust soot load downstream (74b) of the PF or the upstream soot exposure of the PF may be determined. The upstream exposure rate of soot may be used for calculation of PF load (amount of weight of soot in the filter for purposes of regeneration/cleaning of the filter, or it may be used to assist with the calculation of PF efficiency, and the downstream soot concentration may be thereby used to diagnose and monitor the health and functioning of the PF (on-board diagnosis). Connecting wires 222 and 224 may extend through a support structure (e.g., support structure 201 of FIG. 2A). Alternatively, if the PM sensor 201 is upstream of the PF and so measuring unfiltered feedgas exhaust from the engine, the accumulating rate of load on the sensor may be used for engine control (with or without a PF) and also it may be used assist in the calculation of a percent efficiency of the PF for removing PM. Thus, a PF may not be arranged in the exhaust passage.

As shown, each of the positive 217 and negative 218 electrodes are substantially circular and are concentric with the first central axis 296. The positive 217 and negative 218 electrodes may not contact one another. A distance between the positive 217 and negative 218 electrodes may be between 10-70 micrometers. In some examples, the distance may be between 20-60 micrometers. The distance may be uniform throughout an entire circumference of each of the positive 217 and negative 218 electrodes.

Additionally or alternatively, the distance may vary in gap if a variation may create electrostatic amplification of the electrostatic field. The gap may be gradated, so as to lengthen the conductive slope time of the sensor (e.g., a portion of a measurement time where the conduction current rises) One factor effecting gap width between the positive 217 and negative 218 electrodes may include soot fibers which may grow across the gap more quickly if the gap is small, but an advantage of a larger gap is higher immunity to false load estimation due to larger particulate matter. The PM sensor 74 may allow the gap to be smaller by allow the inertia of larger particulate matter 286 to flow uninterruptedly through the PM sensor 74 without impinging onto the electrodes. Also, a lower incidence of the large conductive particles 286 may decrease positive current spikes in the signal and so the sensor signal availability is improved.

A first flow deflector 262 and a second flow deflector 264 may be arranged in the disc portion 210. The first flow deflector 262 may be arranged upstream of the positive electrode 217 such that exhaust gas may contact the first flow deflector before it reaches the positive electrode. The second flow deflector 264 may be arranged between the positive 217 and negative 218 electrodes. As such, the second flow deflector 264 may be downstream of the positive 217 electrode and upstream of the negative electrode 218. The first and second flow deflectors 262,264 may force exhaust gas to flow in a zig-zag, sinusoidal, undulating, or similar pattern before flowing through the at least one second opening 212 of the disc portion 210.

The first flow deflector 262 and the second flow deflector 264 may be similar in shape, wherein both may be circular. The first flow deflector 262 and the second flow deflector 264 may be physically coupled to opposite surfaces of the disc portion 210. That is to say, the first flow deflector may be coupled to a downstream facing surface 268 and the second flow deflector 264 may be coupled to an upstream facing surface 266. A distance between the first flow deflector 262 and the upstream facing surface 266 may be between 1-5 millimeters. In some examples, the distance may be between 2-4 millimeters. In one example, the distance is exactly 3 millimeters. The distance may be space in which exhaust gas may flow around the first flow deflector 262 toward the positive electrode. The second flow deflector 264 may be similarly spaced away from the downstream facing surface 268. Furthermore, a distance between the first flow deflector 262 and the second flow deflector 264 may be substantially constant and equal to the distance between the positive 217 and negative 218 electrodes.

Herein, a flow of exhaust gas through the exhaust passage 148 to the PM sensor 74 is described. Exhaust gas flow is shown via arrows 280, 282, and 284. Arrows 280 depict exhaust gas flowing proximally to the first central axis 296. Arrows 284 depict exhaust gas flowing proximally to the exhaust pipe of the exhaust passage 148. Said another way, arrows 284 depict exhaust gas flowing distally to the first central axis 296. Thus, arrows 282 represent exhaust gas flowing between the first central axis 296 and the exhaust pipe. Herein, arrows 280, 282, and 284 may be interchangeably referred to as exhaust gas 280, 282, and 284, respectively.

As shown, arrows 282 and 284 include exhaust gas that may not flow into the PM sensor 74. In the example of FIG. 2B, exhaust gas represented by arrows 284 may flow uninterruptedly through the exhaust passage 148 without contacting the PM sensor 74. Exhaust gas represent by arrows 282 may contact the outer shell 202 of the PM sensor 74 and ricochet therefrom. Exhaust gas 282 may then flow toward the exhaust pipe and merge with exhaust gas 284.

Exhaust gas 280, along with larger particulates depicted by circles 286 (herein, larger particulates 286), may enter the PM sensor 74 via the first opening 204. Larger particulates may include water droplets and large particulate matter and/or soot. Larger particulates may decrease an accuracy of the PM sensor 74 by prematurely coupling the positive 217 and negative 218 electrodes. Due to a momentum of the larger particulates 286, they may be less likely to deviate from the first central axis 296. As such, the larger particulates 286 may flow through the PM sensor 74 along the first central axis 296 such that they enter via the first opening 204 and exit via a third opening 208. As shown, the third opening 208 is arranged directly opposite the first opening 204 along the first central axis 296. The third opening 208 may be similarly shaped to the first opening 204. However, a size of the third opening 208 may be larger than the size of the first opening 204. In some examples, the third opening 208 may be 1.1 to 5 times larger than the first opening 204. By flowing out of the third opening 208, the larger particulates may not flow around the disc portion 210 and deposit one or more exhaust gas constituents between the positive 217 and negative 218 electrodes.

Exhaust gas 280 may divide into two portions, a first portion 280A and a second portion 280B. The first portion 280A may flow directly to the third opening 208 without flowing to the positive 217 and negative 218 electrodes. The second portion 280B may follow a shape of the outer surface 202 such that it flows toward the first flow deflector 262. The second portion 280B may navigate around the first flow deflector 262 and deposit particulates onto the substrate 216 at the positive electrode 217. The second portion 280B may then flow between the second flow deflector 264 and the downstream facing wall 268, where it may deposit particulates onto the substrate 216 at the negative electrode 217. The second portion 280B may exit the PM sensor 74 via the at least one second opening 212, wherein the second portion 280B may merge with exhaust gas flowing distally to the first central axis 296.

Turning now to FIG. 2C, it shows a front side 275 of the substrate 216. The positive 217 and negative 218 electrodes are illustrated spanning an entire circumference of the substrate 216. The first flow deflector (e.g., first flow deflector 262 of FIG. 2B) may be arranged between the third opening 208 and the positive electrode 217. The second flow deflector (e.g., second flow deflector 264 of FIG. 2B) may be arranged between the positive electrode 217 and the negative electrode 218.

Turning now to FIG. 2D, it shows a back side 276 of the substrate 216. As shown, the PM sensor element (e.g., PM sensor element 254 of FIG. 2B) may include a heating element 219 integrated into a surface of the sensor substrate 216 opposite the electrodes 220. In alternate embodiments, the PM sensor element 254 may not include a heating element. The heating element 219 may comprise, but is not limited to, a temperature sensor, and a heater. Possible materials for the heater and the temperature sensor forming the heating element 219 may include platinum, gold, palladium, and the like; and alloys, oxides, and combinations comprising at least one of the foregoing materials, with platinum/alumina, platinum/palladium, platinum, and palladium. The heating element 219 may be used for regenerating the PM sensor element 254. Specifically, during conditions when the particulate matter load or soot load of the PM sensor element 254 is higher than a threshold, heating element 219 may be operated to burn accumulated soot particles from the surface of sensor. During PM sensor regeneration, the controller 12 may provide a voltage to a voltage source 230, which is needed for operating the heating element 219. In addition, the controller may close the switch 232 for a threshold time to apply the voltage via the voltage source 230 to the heating element 219 in order to raise the temperature of the heating element 219. Subsequently, when the sensor electrodes are sufficiently clean, the controller may open the switch 232 to stop heating the heating element 219. By intermittently regenerating the PM sensor 201, it may be returned to a condition (e.g., unloaded or only partially loaded condition) more suitable for collecting exhaust soot. In addition, accurate information pertaining to the exhaust soot level may be inferred from the sensor regeneration and this information may be used by the controller for diagnosing leaks in the particulate filter. The sensitivity of the PM sensor may be affected by large particulates and/or water droplets getting deposited on the PM sensor element 254. In addition, the sensitivity of the PM sensor element 254 may further depend on the exhaust flow rate. Higher sensitivity is typically observed at higher exhaust flow, while lower sensitivity occurs at lower exhaust flow. It may be possible to filter out larger particulates and water droplets and obtain a flow independent PM sensor by using a design for the protection tube 250, as described below.

Turning now to FIG. 3, a method 300 for determining if PM sensor element regeneration conditions are met is shown. Instructions for carrying out method 300 and the rest of the methods included herein may be executed by a controller based on instructions stored on a memory of the controller and in conjunction with signals received from sensors of the engine system, such as the sensors described above with reference to FIGS. 1 and 2A-2D. The controller may employ engine actuators of the engine system to adjust engine operation, according to the methods described below.

At 302, method 300 includes determining and/or estimating engine operating conditions. Engine operating conditions determined may include, for example, engine speed, exhaust flow rate, engine temperature, exhaust air-fuel ratio, exhaust temperature, duration (or distance) elapsed since a last regeneration of the PF, PM load on PM sensor, boost level, ambient conditions such as barometric pressure and ambient temperature, etc.

Next at 304, the method includes determining if PM sensor regeneration conditions are met. Specifically, when the PM load on the PM sensor element is greater than a threshold, or when a resistance of the PM sensor drops to a threshold resistance, the PM sensor regeneration conditions may be considered met, and the PM sensor may be regenerated to enable further PM detection. If the PM sensor regeneration conditions are met, then method 300 proceeds to 308 where the PM sensor may be regenerated as described in method 400 of FIG. 4. However, if PM sensor regeneration conditions are not met when checked at 304, then method 300 proceeds to 306, where the PM sensor continues to collect PMs on the PM sensor. As such, any PMs not deposited on the PM sensor is directed out of the PM sensor via the outlet of the PM sensor.

Turning now to FIG. 4, a method 400 for regenerating the PM sensor (such as a PM sensor 74 shown in FIGS. 1 and 2A-2D, for example) is shown. Specifically, when the soot load on the PM sensor is greater than the threshold, or when a resistance of the PM sensor adjusted for temperature drops to a threshold resistance, the PM sensor regeneration conditions may be considered met, and the PM sensor may need to be regenerated to enable further PM detection. At 402, regeneration of the PM sensor may be initiated and the PM sensor may be regenerated by heating up the sensor at 404. The PM sensor may be heated by actuating a heating element coupled thermally to the sensor electrode surface, such as a heating element embedded in the sensor, until the soot load of the sensor has been sufficiently reduced by oxidation of the carbon particles between the electrodes. The PM sensor regeneration may be controlled by using timers and the timer may be set for a threshold duration at 402. Alternatively, the sensor regeneration may be controlled using a temperature measurement of the sensor tip, or by the control of power to the heater, or any or all of these. When the timer is used for PM sensor regeneration, then method 400 may include checking if the threshold duration has elapsed at 406. If the threshold duration has not elapsed, then method 400 proceeds to 408 where the PM sensor regeneration may be continued.

If threshold duration has elapsed, then method 400 proceeds to 410 where the PM sensor regeneration may be terminated and the electric circuit may be turned off at 412. Further, the sensor electrodes may be cooled to the exhaust temperature for example. Method 400 proceeds to 414 where the resistance between the electrodes of the soot sensor is measured. From the measured resistance, possibly compensated for temperature, the PM or soot load of the PM sensor (i.e., the accumulated PMs or soot between the electrodes of the PM sensor) may be calculated at 416 and the method proceeds to 418. At 418, the calculated soot load of the PM sensor may be compared with a threshold, Lower_Thr. The threshold Lower_Thr, may be a lower threshold, lower than the regeneration threshold, for example, indicating that the electrodes are sufficiently clean of soot particles. In one example, the threshold may be a threshold below which regeneration may be terminated. If the soot load continues to be greater than Lower_Thr, indicating that further regeneration may be desired, method 400 proceeds to 408 where PM sensor regeneration may be repeated. However, if the PM sensor continues to undergo repeated regenerations, the controller may set error codes to indicate that the PM sensor may be degraded or the heating element in the soot sensor may be degraded. If the soot load is lower than the threshold Lower_Thr, indicating that the electrode surface is clean, method 400 proceeds to 420, where the soot sensor resistance and regeneration history may be updated and stored in memory. For example, a frequency of PM sensor regeneration and/or an average duration between sensor regenerations may be updated. At 422, various models may then be used by the controller to calculate the percentage efficiency of the PF the filtration of soot. In this way, the PM sensor may perform on-board diagnosis of the PF.

FIG. 5 illustrates an example routine 500 for diagnosing PF function based on the regeneration time of the PM sensor. At 502, it may be calculated by the controller, through calibration, the time of regeneration for the PM sensor, t(i)_regen, which is the time measured from end of previous regeneration to the start of current regeneration of the PM sensor. At 504, compare t(i)_regen to t(i−1) regen, which is the previously calibrated time of regeneration of the PM sensor. From this, it may be inferred that the soot sensor may need to cycle through regeneration multiple times in order to diagnose the PF. If the t(i) regen is less than half the value of t(i−1) region, then at 508 indicate PF is leaking, and PF degradation signal is initiated. Alternatively, or additionally to the process mentioned above, the PF may be diagnosed using other parameters, such as exhaust temperature, engine speed/load, etc. The degradation signal may be initiated by, for example, a malfunction indication light on diagnostic code.

A current regeneration time of less than half of the previous regeneration time may indicate that the time for electric circuit to reach the R_regen threshold is shorter, and thus the frequency of regeneration is higher. Higher frequency of regeneration in the PM sensor may indicate that the outflowing exhaust gas is composed of a higher amount of particulate matter than realized with a normally functionally PF. Thus, if the change of regeneration time in the soot sensor reaches threshold, t_regen, in which the current regeneration time of the PM sensor is less than half of that of the previous regeneration time, a PF degradation, or leaking, is indicated, for example via a display to an operator, and/or via setting a flag stored in non-transitory memory coupled to the processor, which may be sent to a diagnostic tool coupled to the processor. If the change of regeneration time in the soot sensor does not reach threshold t_regen, then at 506 PF leaking is not indicated. In this way, leaks in a particulate filter positioned upstream of the particulate matter sensor may be detected based on a rate of deposition of the particulates on the particulate matter sensor element.

In this way, a PM sensor may be arranged in an exhaust passage such that it may receive sufficient amount of exhaust gas during periods of low and high exhaust gas flow rates. The PM sensor further comprises features for mitigating impingement of larger particulates onto its electrodes, which may increase an accuracy of diagnosing an upstream particulate filter. The technical effect of arranging the varying diameter cone-shaped PM sensor in a central region of the exhaust passage is to enable the PM sensor to receive sufficient exhaust gas flow through a plurality of engine operating conditions without introduction of an actuator while also allowing the sensor to independently prevent larger particulate deposition. Thus, a cheap, easy-to-manufacture, and easy-to-install PM sensor may be incorporated into an exhaust passage to increase diagnostics of an upstream PF.

An example of a method comprises flowing exhaust gas proximal to a central axis of an exhaust passage through a first opening of a cone-shaped soot sensor; expelling a first portion of the exhaust gas through a second opening directly across the first opening, and diverting a second portion of the exhaust gas around flow diverters spaced about electrodes distal to the central axis. A first example of the method further includes where the electrodes are coupled to a substrate capturing particulates from the second portion of exhaust gas. A second example of the method, optionally including the first example, further includes where the second portion of exhaust gas flows in a radially outward direction perpendicular to the central axis through a plurality of outlets arranged along a disc portion of the soot sensor. A third example of the method, optionally including the first and/or second examples, further includes where the first portion of exhaust gas comprises larger particulates than the second portion of exhaust gas. A fourth example of the method, optionally including one or more of the first through third examples, further includes where diverting the second portion further includes flowing the second portion of exhaust gas in a sinusoidal pattern around a first flow diverter and a second flow diverter. A fifth example of the method, optionally including one or more of the first through fourth examples, further includes where the first portion of exhaust gas flow linearly and the second portion of exhaust gas zig-zags.

An embodiment of a particulate matter sensor comprises a cone-shaped outer shell comprising a hollow interior with a first opening admitting exhaust gas thereto, a disc-portion of the outer shell includes a first flow deflector coupled to a first surface and a second flow deflector coupled to a second surface, and a plurality of second openings configured to expel exhaust gas from the disc-portion to an exhaust passage in a direction perpendicular to a general direction of exhaust gas flow. A first example of the particulate matter sensor further includes where the cone-shaped outer shell further comprises a third opening arranged directly opposite the first opening, and where a central axis of the exhaust passage extends through geometric centers of the first and third openings. A second example of the particulate matter sensor, optionally including the first example, further includes where the first opening and third opening are circular, and where a diameter of the first opening is less than a diameter of the third opening. A third example of the particulate matter sensor, optionally including the first and/or second examples, further includes where the first flow deflector is arranged upstream of both a positive electrode and a negative electrode, and where the second flow deflector is arranged between the positive electrode and the negative electrode. A fourth example of the particulate matter sensor, optionally including one or more of the first through third examples, further includes where the first flow deflector is spaced away from the second surface by 1 to 5 millimeters, and where the second flow deflector is spaced away from the first surface by 1 to 5 millimeters. A fifth example of the particulate matter sensor, optionally including one or more of the first through fourth examples, further includes where the first flow deflector and the second flow deflector flow exhaust gas in a sinusoidal pattern before flowing the exhaust gas through one of the plurality of second openings. A sixth example of the particulate matter sensor, optionally including one or more of the first through fifth examples, further includes where a support structure cantilevers the outer shell in the exhaust passage. A seventh example of the particulate matter sensor, optionally including one or more of the first through sixth examples, further includes where the outer shell is symmetric and where the first flow deflector and the second flow deflector are concentric about a central axis of the exhaust passage. An eighth example of the particulate matter sensor, optionally including one or more of the first through seventh examples, further includes where a diameter of the outer shell increases in a downstream direction relative to the general direction of exhaust gas flow, and where the first opening is arranged at an apex of the outer shell.

An embodiment of a system comprises an engine coupled to an exhaust passage, a cone-shaped soot sensor comprising a first opening at its apex admitting exhaust gas from the exhaust passage, a plurality of second openings and a third opening configured to expel exhaust gas from a hollow interior of the cone-shaped soot sensor, and a controller with computer-readable instructions stored on non-transitory memory thereof that when executed enable the controller to regenerate a substrate of the cone-shaped soot sensor in response to a measured resistance by activating a heating element. A first example of the system further includes where the measured resistance corresponds to a resistance of electrodes coupled to a first surface of the substrate and where the heating element is coupled to a second surface of the substrate. A second example of the system, optionally including the first example, further includes where the first and third openings are arranged along a central axis of the exhaust passage, and where the plurality of second openings are distal to the central axis. A third example of the system, optionally including the first and/or second examples, further includes where the plurality of second openings are arranged along a disc portion of the cone-shaped soot sensor, and where the plurality of second openings expel exhaust gas from the disc portion in a radially outward direction toward surfaces of an exhaust pipe of the exhaust passage. A fourth example of the system, optionally including one or more of the first through third examples, further includes where the cone-shaped soot sensor is immovable and where there are no additional inlets or other outlets other than the first opening, plurality of second openings, and the third opening.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
flowing exhaust gas proximal to a central axis of an exhaust passage through a first opening of a cone-shaped soot sensor; expelling a first portion of the exhaust gas through a second opening directly across the first opening, and diverting a second portion of the exhaust gas around flow diverters spaced about electrodes distal to the central axis.

2. The method of claim 1, wherein the electrodes are coupled to a substrate capturing particulates from the second portion of exhaust gas.

3. The method of claim 1, wherein the second portion of exhaust gas flows in a radially outward direction perpendicular to the central axis through a plurality of outlets arranged along a disc portion of the soot sensor.

4. The method of claim 1, wherein the first portion of exhaust gas comprises larger particulates than the second portion of exhaust gas.

5. The method of claim 1, wherein diverting the second portion further includes flowing the second portion of exhaust gas in a sinusoidal pattern around a first flow diverter and a second flow diverter.

6. The method of claim 1, wherein the first portion of exhaust gas flow linearly and the second portion of exhaust gas zig-zags.

7. A particulate matter sensor, comprising:
a cone-shaped outer shell comprising a hollow interior with a first opening admitting exhaust gas thereto;
a disc-portion of the outer shell includes a first flow deflector coupled to a first surface and a second flow deflector coupled to a second surface; and
a plurality of second openings configured to expel exhaust gas from the disc-portion to an exhaust passage in a direction perpendicular to a general direction of exhaust gas flow.

8. The particulate matter sensor of claim 7, wherein the cone-shaped outer shell further comprises a third opening arranged directly opposite the first opening, and where a central axis of the exhaust passage extends through geometric centers of the first and third openings.

9. The particulate matter sensor of claim 8, wherein the first opening and third opening are circular, and where a diameter of the first opening is less than a diameter of the third opening.

10. The particulate matter sensor of claim 7, wherein the first flow deflector is arranged upstream of both a positive electrode and a negative electrode, and where the second flow deflector is arranged between the positive electrode and the negative electrode.

11. The particulate matter sensor of claim 7, wherein the first flow deflector is spaced away from the second surface by 1 to 5 millimeters, and where the second flow deflector is spaced away from the first surface by 1 to 5 millimeters.

12. The particulate matter sensor of claim 7, wherein the first flow deflector and the second flow deflector flow exhaust gas in a sinusoidal pattern before flowing the exhaust gas through one of the plurality of second openings.

13. The particulate matter sensor of claim 7, wherein a support structure cantilevers the outer shell in the exhaust passage.

14. The particulate matter sensor of claim 7, wherein the outer shell is symmetric and where the first flow deflector and the second flow deflector are concentric about a central axis of the exhaust passage.

15. The particulate matter sensor of claim 7, wherein a diameter of the outer shell increases in a downstream direction relative to the general direction of exhaust gas flow, and where the first opening is arranged at an apex of the outer shell.

16. A system, comprising:
an engine coupled to an exhaust passage;
a cone-shaped soot sensor comprising a first opening at its apex admitting exhaust gas from the exhaust passage, a plurality of second openings and a third opening configured to expel exhaust gas from a hollow interior of the cone-shaped soot sensor; and
a controller with computer-readable instructions stored on non-transitory memory thereof that when executed enable the controller to:
regenerate a substrate of the cone-shaped soot sensor in response to a measured resistance by activating a heating element.

17. The system of claim 16, wherein the measured resistance corresponds to a resistance of electrodes coupled to a first surface of the substrate and where the heating element is coupled to a second surface of the substrate.

18. The system of claim 16, wherein the first and third openings are arranged along a central axis of the exhaust passage, and where the plurality of second openings are distal to the central axis.

19. The system of claim 16, wherein the plurality of second openings are arranged along a disc portion of the cone-shaped soot sensor, and where the plurality of second openings expel exhaust gas from the disc portion in a radially outward direction toward surfaces of an exhaust pipe of the exhaust passage.

20. The system of claim 16, wherein the cone-shaped soot sensor is immovable and where there are no additional inlets or other outlets other than the first opening, plurality of second openings, and the third opening.

* * * * *